United States Patent [19]

Olsen

[11] 4,046,011

[45] Sept. 6, 1977

[54] ONE-WAY VALVE FOR FLUID SAMPLER DEVICE

[76] Inventor: Donald W. Olsen, 850 Kees, Lebanon, Oreg. 97355

[21] Appl. No.: 700,854

[22] Filed: June 29, 1976

[51] Int. Cl.² .................... G01N 1/14; F16K 15/04
[52] U.S. Cl. ................................ 73/421 B; 137/843
[58] Field of Search .................... 73/421 B; 137/843

[56] References Cited

U.S. PATENT DOCUMENTS

| | | | |
|---|---|---|---|
| 2,214,346 | 9/1940 | Pim | 137/843 |
| 3,465,595 | 9/1969 | Tansony | 73/421 B |
| 3,720,109 | 3/1963 | Blechman | 73/421 B |
| 3,788,145 | 1/1974 | Irwin | 73/421 B |

*Primary Examiner*—S. Clement Swisher
*Attorney, Agent, or Firm*—Clarence A. O'Brien; Harvey B. Jacobson

[57] ABSTRACT

A one-way valve for liquid sampler devices and the like which has an effective self-cleaning function for use in sampling liquid or gas fluids containing solids and sticky material. The valve and seat are in a housing where a desired liquid or gas to be sampled is passed with the valve permitting flow in one direction only. The seal will close the input to the housing when flow is attempted in the other direction and prevents same. The valve is of concave shape and made of soft pliable material such as rubber. The valve seat is essentially a flat round disc with a smooth surface and an inlet hole in the center. The soft pliable material valve lays on the seat, unattached, with the outer edges touching the flat seating surface. The concave shape of the valve allows the incoming material to exert its pressure over a large area of the valve, to give maximum lifting force to the valve. This extra force is important when sticky or gummy material is present and on the seat. When the sample has been taken and the valve flattens, the outer rim expands and performs a wiping action with the rim edge against the seat. This wiping action cleans the sealing surface to effect a positive seal. The valve has specific application with sampling devices having pulse relay operators of the pneumatic type.

11 Claims, 5 Drawing Figures

ONE-WAY VALVE FOR FLUID SAMPLER DEVICE

BACKGROUND OF THE INVENTION

1. Field of the Invention

This invention relates generally to one-way inlet valves for liquid and for use with sampling devices, and especially for samplers of the pneumatic pulse relay operator type.

2. Description of the Prior Art

A common problem with known prior one-way valve structures is that many of them will function with air or gas flow but not with liquid.

Another known problem is that many one-way valves are mechanically operated and require some positive actuating mechanism attached thereto for their proper operation.

Another problem is that many of the known type valves are not automatically operating for a one-way type operation.

Another problem with known type devices is that the valves are not self-cleaning and are not usable with materials which are sticky or gummy, or with the sampling of liquid or gas fluids containing solids.

Known prior art patents which may be pertinent to this invention are as follows:

| | | |
|---|---|---|
| 2,622,792 | A.E. Ramclow | Dec. 23, 1952 |
| 3,159,176 | N.A. Russell et al | Dec. 1, 1964 |
| 3,539,150 | R.F. Conrad | Nov. 10, 1970 |
| 3,550,614 | C.E.T. Englund | Dec. 29, 1970 |
| 3,800,817 | K.H. Gropp | April 2, 1974 |

None of these known prior art devices offers the new and unique features of the invention disclosed herein.

SUMMARY OF THE INVENTION

An object of the present invention is to provide a nonreturn or one-way valve for use with devices for sampling liquids or gas containing solids and/or sticky material.

Another object of the present invention is to provide a one-way valve which is self-cleaning and may be used with materials having solid particles and gummy materials contained therein with said valve functioning to effectively clean the valve seat of such contaminants upon operation of same.

A further object of this invention is to provide a valve and valve seat with the valve being made of soft pliable material and of concave shape. This permits a greater surface area for contact by the fluid being sampled and for the operating pressure thereof to open said valve, and to more effectively function to clean the valve seat when the valve closure action takes place. Since the valve itself is soft and flexible, the closure action also will be more effective than with conventional type valves.

A still further object of this invention is to provide a one-way valve structure in combination with a fluid sampling device of the pneumatic pulse relay control type in order to periodically sample fluids containing contaminants therewithin and in order to secure such samples for testing purposes.

The one-way valve for fluid sampling devices of this invention is usable for sampling liquids or gases which contain solids, gummy or sticky materials. Conventional type one-way valves are made of rigid material, and do not seal properly when solid particles get between the valve and its seat. The valve herein is made of a soft pliable material such as rubber and it is concave shaped. The valve seat is a flat round disc with a smooth surface and an inlet hole in the center thereof. The valve and seat are placed in a housing normally associated with the sampling device structure where it is desired to pass liquid or gas in one direction and seal bubble tight in the opposite direction. The valve lays on the seat, unattached, with the outer edges touching the flat seating surface. The concavity of the valve allows the incoming fluid material to exert its pressure over a large area of the valve surface, in order to give maximum lifting force to open the valve. This extra force is important when sticky or gummy material is present on the seat. Such material tending to adhere or stick the valve to its closed position.

Some very important features of the device of this invention are in the fact that the light weight of the valve member offers a very small resistance to fluid flow through the valve. The concave shape of the valve allows the inlet pressure to apply more force to open the valve, and in the case of sticky material tending to stick the valve to its seat. A collapsing action of the valve due to its unique design tends to wipe the sealing surface clean. Therefore, any contaminants or sticky substances on the valve seat will after operation of the valve be loosened and removed. A double seal is also formed when the valve is closed, one on the outer rim of the valve member itself, and one on the inner portion which is directly over the inlet opening. No mechanical hinges or joints are present to bind in case of applications under corrosive condition, such as when used with fluids which have corrosive contaminants contained therein or which are inherently corrosive in and of themselves.

The fluid sampling device with which this valve is specifically to be associated is preferably of the pneumatic pulse relay operator type which periodically will sample the fluid and pass or pump same on to a further point of testing.

These, together with other objects and advantages which will become subsequently apparent, reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
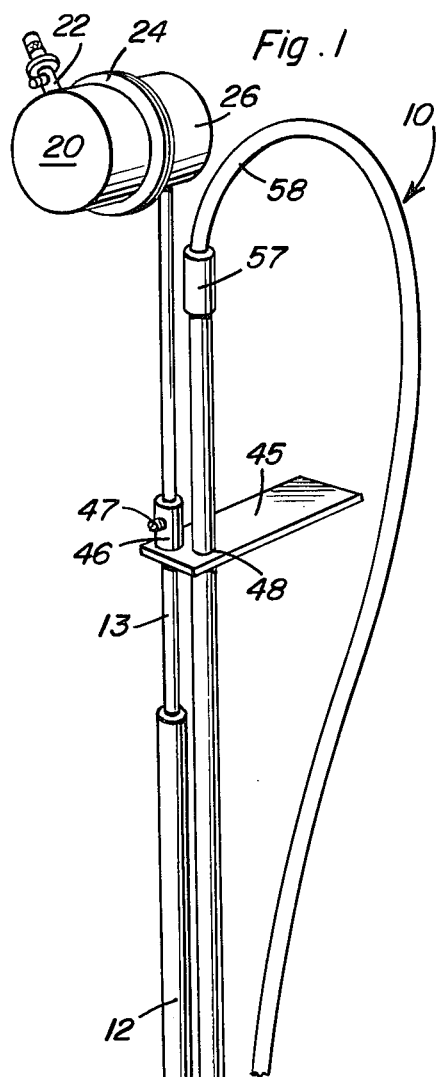
FIG. 1 is a perspective view of a fluid sampler incorporating the valve of this invention.

Referring to FIG. 1 of the drawings, reference numeral 10 indicates in general, the fluid sampling device with one-way valve of this invention. The sampler device comprises a main sample chamber tube 12 connected by means of a reduced section tube 13 and mounted atop thereof a pulse relay of the pneumatic type 20, 26. A sample outlet tube 14 is also provided with the one-way valve structure connecting the tubes 12 and 14 at the lower end thereof. This one-way structure 16 is shown in greater detail in FIGS. 2, 3 and 4. The overall sampler structure is fabricated from non-corrosive stainless steel for use with fluids of corrosive nature if desired.

Continuing with our description of the overall sampler device of FIG. 1; mounted adjustably along tube 13 is a structure for attachment of the overall device to outside support structure. This attachment structure 45 is mounted upon tube 13 by means of the sleeve 46 which is securely fastened to plate 45 and has an adjusting set screw 47 provided therein. Another aperture 48 is aligned with and slides over the outlet tube 14. Thus, as is obvious, in use the bracket 45 may be attached to a positive support structure adjacent the sampling point and the position of the tubes 12 and 14 together with the connecting one-way valve structure 16 adjusted so that the lower aperture 18 for the valve 16 is at the appropriate depth and position within the liquid being sampled.

In order to effect the operation of the sampling device a pneumatic pulse relay 20, 26 is provided. This structure is normally cast from aluminum and coated inside with epoxy. Once supplied with compressed air, the relay will deliver a distinct pulse of air to the sampler at adjustable intervals.

Looking at FIGS. 2, 3 and 4, the one-way valve will now be described in detail. The primary housing 16 has mounted therein by screw threads 19 or the like a plug 17. This plug 17 is provided with a central hole or aperture 18. At least the inner surface of the plug 17 is of smooth surface material, preferably also of stainless steel. Normally, unless contaminants such as solid particles or sticky or gummy material is being tested, the valve member 50 may be of teflon in the shape of a wafer. However, when testing some types of fluid materials having contaminants therein, such a teflon wafer will tend to stick or bind. This defeats, of course, the overall operation of the sampler device.

Figure 2:
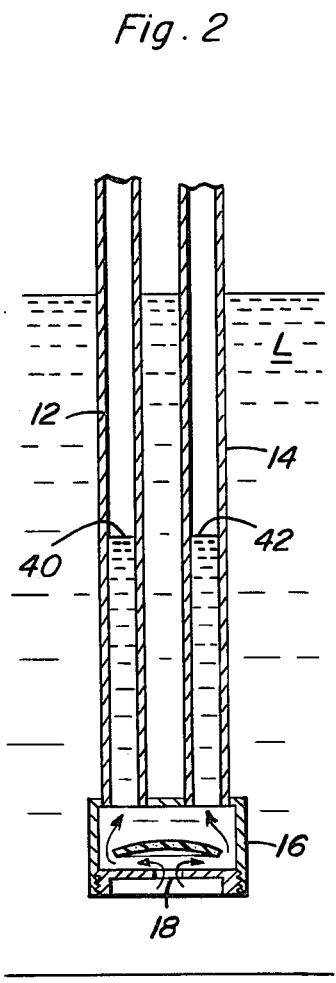
FIG. 2 is a side elevational view, in cross section, of the lower end of the sampler device showing the one-way valve of this invention in open position.
Figure 3:
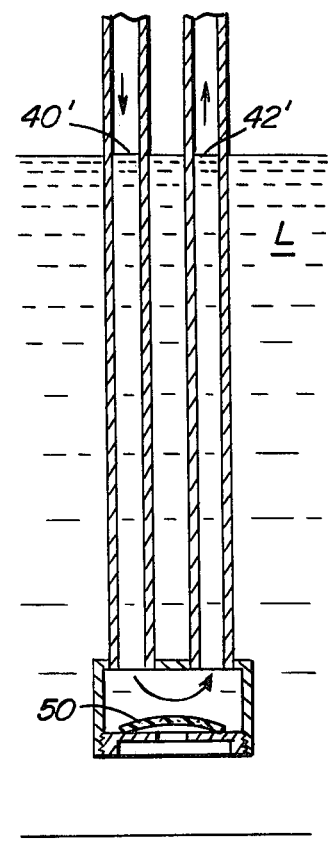
FIG. 3 is a side elevational view, in cross section, of the lower end of the sampler device showing the valve of this invention in initial closing position.
Figure 4:
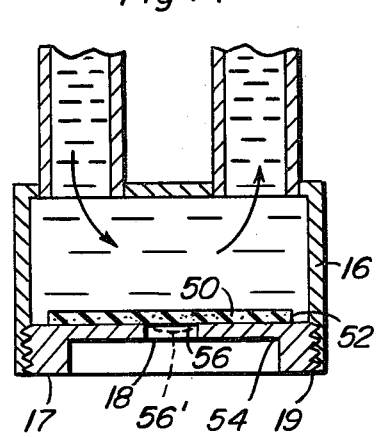
FIG. 4 is an enlarged cross-sectional view of the valve arrangement of FIGS. 2 and 3 showing the valve as completely closed.

Improved valve member 50 disclosed herein is as shown in FIGS. 2 and 3, of normally concave shape and is made of a soft flexible material such as rubber. As can be seen in FIG. 2, normally the valve 50 will be lifted upwardly by the pressure of the fluid being sampled so that said fluid, in this case a liquid L, will rise within the tubes 12 and 14 and have a surface level at the initial start 40 and 42. When the level of the liquid within the tubes 12 and 14 reaches that of the level of the liquid outside of said tubes, such as viewed in FIG. 3, and indicated by 40' and 42', liquid flow stops. At this point, the valve 50 will settle back onto the inner surface of seat member 17 and over the inlet port 18. Then when the input pulse is applied from the pulse relay 20, 26 through the tube 13 into tube 12, pressure will be greater on top of the valve 50, as best seen in FIG. 4 and indicated by small flow arrows on the drawing, and the concave shape valve member structure will flatten with a self-cleaning action of the edges 52, 54. This sliding action of the outer rim and bottom edge 54 of the valve member 50 performs a wiping action against the valve seat. This wiping action tends to clean the seating surface in order to remove any contaminants such as solid particles or sticky particles, and is in effect a self-cleaning action in order to permit a positive seal. While a positive seal is present between the lower surface of the valve member 50 and the upper surface of the valve seat 17 at the aperture 18, the force atop said member will also tend to slightly bubble or push the center portion of the valve member into the inlet aperture 18 and effectively form a seal around said aperture. This is indicated on the FIG. 4 by reference numeral 56 and dotted lines 56'.

Figure 5:
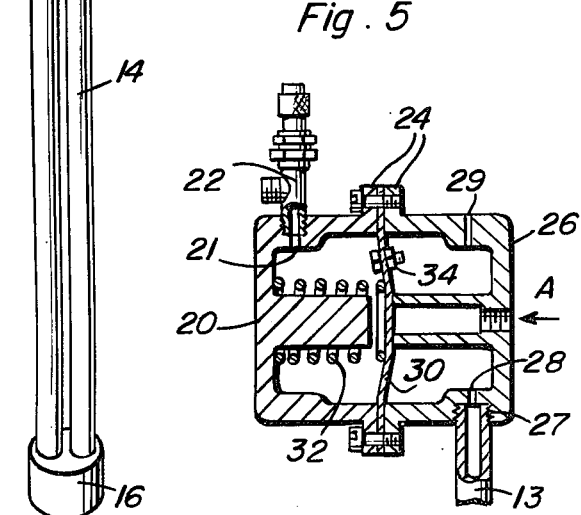
FIG. 5 is a side view, in cross section, of the control relay structure for actuation of the sampler and as shown at the top of same in FIG. 1.

The pulse relay unit for operating the sampler device, of this invention, is shown in detail in FIG. 5. The relay housing comprises two parts 20 and 26 having appropriate flange portions 24 which are connected by conventional type screws or bolts. Between said flanges is a flexible diaphragm member 30. The diaphragm also is provided with a check valve 34. Diaphragm spring 32 and an inlet pneumatic air port A are also shown. An outlet aperture 27 is threadedly connected to the upper end of tube 13 together with appropriately sized opening 28 for air pulse jet from the relay. Another bleeder aperture 29 is also provided in the member 26. An adjustable needle valve 22 is appropriately mounted in a tapped aperture 21 in the housing 20.

The overall operation of the sampling device is as follows: at the start of a sampling cycle, liquid or other fluid flows through the inlet port 18, displacing the inlet valve 50, and rises in the sample chamber and outlet, to the height of liquid flowing through the sampling structure, such as a flume or weir.

Air pressure in the control chamber of the pneumatic pulse relay 20, 26 holds the diaphragm over the air supply port A. This pressure slowly bleeds to the atmosphere through the needle valve 22 which is adjustable. When the pressure in the control chamber bleeds low enough, the diaphragm moves away from the air inlet port A, allowing air to enter the sample chamber and pass through the tube 13 in a pulse manner. Air pressure exerted upon the liquid in the sample chamber tube 12 will force the liquid downwardly and will seat and seal the inlet valve member 50, and force the fluid sample out the outlet tube 14 to a sample container through the connector 57 and outlet tube 58. When the sample is expelled the air pressure will completely flatten the concave valve member 50 to clean and seal, as seen in FIG. 4 and as already described above.

While this action is taking place some of the air in the chamber of housing 26 flows through the check valve 34 into the control chamber within housing 20. When the air pressure in the control chamber of housing 20 is equal to the pressure in the operating chamber, the spring forces the diaphragm back over the air inlet A. The air is now shut off and the sample again rises in the sample chamber of tube 12, ready for the next cycle. Air consumption is approximately 0.05 cubic feet of free air per cycle. By adjusting the needle valve 22, the repetitive rate of the sampling device may be varied.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A fluid sampler device with one-way valve comprising; first means for sampling fluid, second means for controlling the frequency of sampling in a repetitive manner, and third means for effecting a one-way flow of the fluid being sampled, said first means including a sample chamber, and the third means including a valve chamber for the fluid sample, an inlet thereto, and a sample outlet therefrom, and the third means further including a flexible valve member which normally takes on a concave shape when the valve is passing fluid, and assumes a flat plane shape when the fluid flow is stopped and the valve is closed. and fourth means associated with the flexible valve to effect the cleaning action of a valve seat within the valve chamber.

2. The structure as set forth in claim 1, wherein the fourth means consists of the edge of the flexible valve member which scraps the inner valve seat portion of the valve chamber when the flexible valve member goes from the convex shape to the flat plane shape with each operation of the overall device.

3. The structure as set forth in claim 2, wherein the valve sample chamber has associated therewith a pulse relay means for effecting the repetitive sample operation.

4. The structure as set forth in claim 3, wherein the pulse relay means includes a pneumatic operator diaphragm and check valve structure connected to a pneumatic source in order to effect said repetitive function of the second means.

5. The structure as set forth in claim 4, wherein the pulse relay means further includes a spring bias for the diaphragm and an adjustable bleed needle valve to permit a slow flow of air out of the pulse relay means in order to adjust the repetitive rate of the structure.

6. A fluid sampler device with one-way valve comprising; first means for sampling fluid, second means for controlling the frequency of sampling in a repetitive manner, and third means for effecting a one-way flow of the fluid being sampled, said first means including a sample chamber, and the third means including a valve chamber for the fluid sample, an inlet thereto, and a sample outlet therefrom, and the third means further including a flexible valve member which normally takes on a concave shape when the valve is passing fluid, and assumes a flat plane shape when the fluid flow is stopped and the valve is closed, and fourth means associated with the flexible valve to effect the cleaning action of a valve seat within the valve chamber, the fourth means consisting of the edge of the flexible valve member which scraps the inner valve seat portion of the valve chamber when the flexible valve member goes from the convex shape to the flat plane shape with each operation of the over-all device, the valve sample chamber having associated therewith a pulse relay means for effecting the repetitive sample operation, the pulse relay means including a pneumatic operator diaphragm and check valve structure connected to a pneumatic source in order to effect said repetitive function of the second means, the pulse relay means further including a spring bias for the diaphragm and an adjustable bleed needle valve to permit a slow flow of air out of the pulse relay means in order to adjust the repetitive rate of the structure, and the device including two substantially parallel elongated tubes connected at the bottom thereof to the valve sample chamber, one of said tubes being connected to the pulse relay means at the top thereof, and the other elongated tube being connected to a sample outlet at the top thereof.

7. The structure as set forth in claim 6, together with height adjuster means associated with the aforesaid structure.

8. The structure as set forth in claim 7, wherein the height adjuster means includes a sleeve member about at least one of the tubes, and a set screw adjustment thereon for securing the position of the tube and sampler device within the sleeve member, and a sleeve plate member for connection to an associated support.

9. A one-way valve structure for use with fluids containing contaminants therein comprising; a two-part housing screwed together and having inlet and outlet passageways, a valve seat contained therein and associated with the inlet passageway, and valve means for closing the inlet and in association with the valve seat for effecting a cleaning action thereof to remove any contaminants deposited thereon from the fluid flowing therethrough.

10. The structure set forth in claim 9, wherein the valve means includes a member of flexible material larger than the inlet passageway, normally of concave shape, and which under pressure will effectively flatten so the edges thereof will clean the valve seat.

11. The structure as set forth in claim 10, wherein the valve seat is removably secured within the valve housing.

* * * * *